(12) United States Patent
Pichereau et al.

(10) Patent No.: US 12,108,986 B2
(45) Date of Patent: Oct. 8, 2024

(54) METHOD FOR AUTOMATICALLY ASSESSING THE NEAR VISION ACCOMMODATIVE STATE OF A NON-PRESBYOPIC INDIVIDUAL AND ASSOCIATED DEVICE

(71) Applicant: SIVIEW, Marcoussis (FR)

(72) Inventors: Laure Pichereau, Marcoussis (FR); Kelly Woog, Chevry-Cossigny (FR)

(73) Assignee: SIVIEW, Marcoussis (FR)

( * ) Notice: Subject to any disclaimer, the term of this patent is extended or adjusted under 35 U.S.C. 154(b) by 492 days.

(21) Appl. No.: 17/619,494

(22) PCT Filed: Jun. 15, 2020

(86) PCT No.: PCT/EP2020/066470
§ 371 (c)(1),
(2) Date: Dec. 15, 2021

(87) PCT Pub. No.: WO2020/254239
PCT Pub. Date: Dec. 24, 2020

(65) Prior Publication Data
US 2022/0409042 A1    Dec. 29, 2022

(30) Foreign Application Priority Data
Jun. 19, 2019 (FR) ........................... 1906593

(51) Int. Cl.
*A61B 3/09* (2006.01)
*A61B 3/032* (2006.01)
*A61B 3/04* (2006.01)

(52) U.S. Cl.
CPC ............... *A61B 3/09* (2013.01); *A61B 3/032* (2013.01); *A61B 3/04* (2013.01)

(58) Field of Classification Search
CPC .............. A61B 3/09; A61B 3/032; A61B 3/04
USPC ....................................................... 351/233
See application file for complete search history.

(56) References Cited

U.S. PATENT DOCUMENTS

| | | | | | |
|---|---|---|---|---|---|
| 6,045,225 | A | * | 4/2000 | Hosoi | A61B 3/0285 351/200 |
| 6,048,064 | A | * | 4/2000 | Hosoi | A61B 3/028 351/212 |
| 2012/0188504 | A1 | * | 7/2012 | Petignaud | G02C 7/061 351/159.74 |

FOREIGN PATENT DOCUMENTS

| | | |
|---|---|---|
| FR | 3 050 922 A1 | 11/2017 |
| WO | WO 2018/110731 A1 | 6/2018 |

OTHER PUBLICATIONS

International Search Report as issued in International Patent Application No. PCT/EP2020/066470, dated Aug. 11, 2020.

* cited by examiner

*Primary Examiner* — James R Greece
(74) *Attorney, Agent, or Firm* — Pillsbury Winthrop Shaw Pittman LLP

(57) ABSTRACT

A method for automatically assessing the near vision accommodative state of a non-presbyopic individual, the method being carried out by computer and performed after an assessment of the individual's far vision leading to the generation of a far vision assessment report, includes generating a near vision assessment report optionally including at least one recommendation dependent on the far vision assessment report.

10 Claims, 2 Drawing Sheets

[Fig. 1]
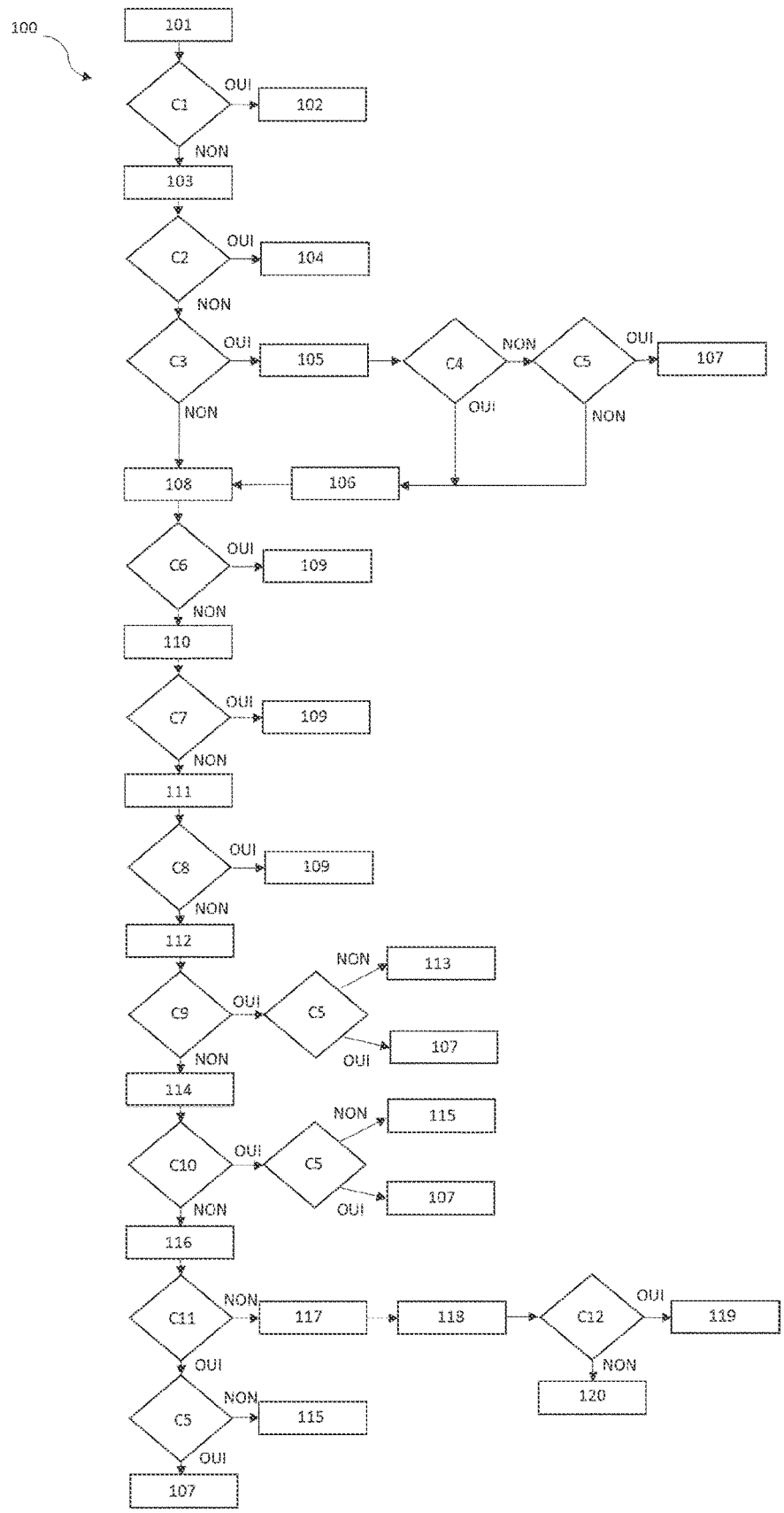

[Fig. 2]
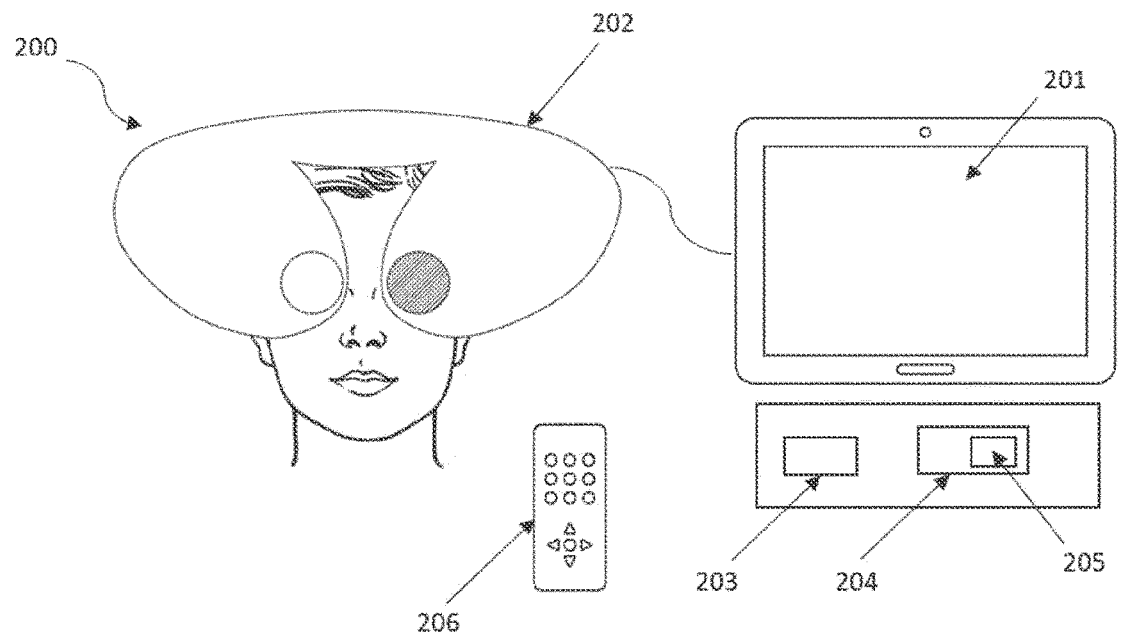

METHOD FOR AUTOMATICALLY ASSESSING THE NEAR VISION ACCOMMODATIVE STATE OF A NON-PRESBYOPIC INDIVIDUAL AND ASSOCIATED DEVICE

CROSS-REFERENCE TO RELATED APPLICATIONS

This application is the U.S. National Stage of PCT/EP2020/066470, filed Jun. 15, 2020, which in turn claims priority to French patent application number 1906593 filed Jun. 19, 2019. The content of these applications are incorporated herein by reference in their entirety.

TECHNICAL FIELD OF THE INVENTION

The technical field of the invention is that of methods for assessing the near vision accommodative state of a non-presbyopic individual.

The present invention relates to a method for assessing the near vision accommodative state of a non-presbyopic individual and in particular a method for automatically assessing the near vision accommodative state of a non-presbyopic individual. The present invention also relates to a device, a computer program product and a recording medium.

TECHNOLOGICAL BACKGROUND OF THE INVENTION

To date, due to a lack of time and/or practice, the near vision examination is almost exclusively carried out on presbyopic subjects, that is subjects over 40 years old, whose accommodative state has deteriorated with age and who need a near vision correction.

However, it is common for young subjects to suffer from problems of over-accommodation or under-accommodation. As these problems affect far vision, these young subjects are often misdiagnosed, which often leads to poor management of their far vision, when they could be managed for near vision, thus avoiding accentuating their far and near vision complaints.

The near vision examination consists, among other things, in assessing the accommodative state of the subject and, in particular, the flexibility of the accommodation/convergence relationship. Two types of capabilities are generally tested: motor capabilities, requiring the subject to bring into play a progressive variation of accommodation (step of 0.25 dioptres) on a fixed convergence plane and phasic capabilities requiring the subject to bring into play an instantaneous accommodation on a same fixed convergence plane whose step is greater than 0.25 dioptres and commonly of 2.00 dioptres.

Among the near vision tests, the NRA/PRA test for Negative Relative Amplitudes and Positive Relative Amplitudes is one of the tests used by health professionals to assess motor capabilities of a presbyopic or non-presbyopic individual.

This test consists in placing a text corresponding to a visual acuity of 80% of the subject's maximum near vision acuity, at a given distance different according to whether the subject is presbyopic or non-presbyopic, and advancing convex lenses in steps of +0.25 dioptres until the subject perceives the first constant blur (RNA) and then in advancing concave lenses in steps of −0.25 dioptres until the subject perceives the first constant blur (PRA). It is then possible to assess either the addition needed by the presbyopic subject or the flexibility of the accommodation/convergence relationship in the non-presbyopic subject, and more broadly to give indications for the latter on the possible management (addition, visual training, far vision reassessment etc.).

The RNA/PRA test is performed manually by the practitioner and is therefore relatively time consuming, which is incompatible with the management of an increasing number of patients.

For these reasons, practitioners more often prefer the accommodative rock test for non-presbyopes, which consists in alternately placing a convex lens with a value of +2.00 dioptres, and then a concave lens with a value of −2.00 dioptres in front of the subjects eyes. The switch from one lens to another is made as soon as the subject can see clearly and simply a text corresponding to a visual acuity of 80% of his or her maximum acuity, placed 40 cm from its eyes. The number of cycles performed in one minute then allows the individual's phasic capabilities to be assessed.

The accommodative rock test, although faster than the NRA/PRA test, does not give any information on the individual's motor capabilities and does not allow assessment of a possible near vision correction that the subject would need.

There is therefore a need to provide a test that allows assessment of the accommodative state of a young subject, that is both his or her motor and phasic capabilities, which is fast, reliable and automatic.

SUMMARY OF THE INVENTION

The invention provides a solution to the above problems by allowing the automatic assessment of the motor and phasic capabilities of a non-presbyopic subject.

A first aspect of the invention relates to a method for automatically assessing the near vision accommodative state of a non-presbyopic individual; the method being computer-implemented and performed after an assessment of the individual's far vision has led to the preparation of a far vision assessment report; including the following steps performed in order:

Placing at least one optotype at a fixed distance from the individual's eyes:
  If the individual fails to read the optotype, interrupting the method and generating a near vision assessment report including a first initial recommendation;
Placing an initial convex lens with a value within the range [+0.50; +1.00] dioptres in front of the individual's eyes:
  If the individual prefers without the initial lens rather than with the initial lens, interrupting the method and generating a near vision assessment report including a second initial recommendation;
  If the individual can see no difference with or without the initial lens, removing the initial lens:
    If the individual has an adaptation time to see clearly again after removing the initial lens, placing the initial lens;
    Otherwise:
      If the far vision assessment report does not advise a near vision assessment, interrupting the method and generating a near vision assessment report;
      Otherwise, placing the initial lens;
Placing a first convex lens with a value within the range [+0.50; +1.00] dioptres in front of the individual's eyes:

If the individual has blurred vision after placing the first lens, interrupting the method and generating a near vision assessment report including a first recommendation;

Placing a second convex lens with a value within the range [+0.50; +1.00] dioptres in front of the individual's eyes:
If the individual has blurred vision after placing the second lens, interrupting the method and generating a near vision assessment report including a first recommendation;

Placing a third convex lens with a value within the range [+0.25, +0.50] n dioptres in front of the individual's eyes:
If the individual has blurred vision after placing the third lens, interrupting the method and generating a near vision assessment report including a first recommendation;

Placing a fourth convex lens with a value within the range [+0.25; +0.50] dioptres in front of the individual's eyes:
If the individual has blurred vision after placing the fourth lens and:
If the far vision assessment report does not advise a near vision assessment, interrupting the method and generating a near vision assessment report;
Otherwise, interrupting the method and generating a near vision assessment report including a second recommendation;

Placing a fifth convex lens with a value within the range [+0.25; +0.50] dioptres in front of the individual's eyes:
If the individual has blurred vision after placing the fifth lens and:
If the far vision assessment report does not advise a near vision assessment, interrupting the method and generating a near vision assessment report;
Otherwise, interrupting the method and generating a near vision assessment report including a third recommendation;

Placing a sixth convex lens with a value within the range [+0.25; +0.50] dioptres in front of the individual's eyes:
If the individual has blurred vision after placing the sixth lens and:
If the far vision assessment report does not advise a near vision assessment, interrupting the method and generating a near vision assessment report;
Otherwise, interrupting the method and generating a near vision assessment report including a third recommendation;

a Otherwise:
Removing the initial lens and the first, second, third, fourth, fifth and sixth lenses;
Placing a first final convex lens of intermediate correction in front of the individual's eyes and then removing the first final lens and placing a second final convex lens of strong correction in front of the individual's eyes:
If the individual prefers the first final lens to the second final lens or if the individual can see no difference between the first and second final lenses, generating a near vision assessment report including a fourth recommendation;
Otherwise, generating a near vision assessment report including a fifth recommendation.

By virtue of the invention, a practitioner can assess a young subject's accommodative state, namely both motor and phasic capabilities, by performing an alternative of the RNA/PRA test adapted to a non-presbyopic subject and optimised in time. On the one hand, the method according to a first aspect of the invention saves the advancement of the concave lenses because, in the context of the automated test and the information to be collected, advancing the concave lenses does not provide additional elements to the conclusions obtained by advancing the convex lenses. Indeed; a normal to high PRA gives little indication other than the fact that the subject has good accommodation and divergence. A low PRA is almost always synonymous with a need for addition, which will have been defined by the RNA measurement, and associated if needed with a convergence problem which can only be confirmed by other tests. On the other hand, young subjects do not generally have any problems with de-accommodation for convex lenses below 1.50 dioptres. Thus, the method according to a first aspect of the invention advances the first convex lenses with a step within the range [0.50 and 100] dioptres rather than a step of 0.25 dioptres, which thus makes it possible to reduce the time taken to implement the method and to assess, in addition to the motor capabilities assessed by advancing the lenses, the phasic capabilities by greater differences in correction between each lens (step greater than 0.25 dioptres). Moreover, the test is fully automatic, that is it does not require the intervention of the practitioner. Thus, this assessment is non-restrictive and is a diagnostic aid for the practitioner.

In addition to the characteristics just discussed in the preceding paragraph, the method according to a first aspect of the invention may have one or more of the following additional characteristics, considered individually or according to any technically possible combination.

According to an alternative embodiment, the first initial recommendation is to consult an ophthalmologist and/or to perform a near vision assessment on trial glasses.

According to an alternative embodiment compatible with the preceding alternative embodiment, the second initial recommendation is to perform accommodation training exercises and/or to perform a binocular vision assessment.

According to an alternative embodiment compatible with the preceding alternative embodiments, the first recommendation is to perform accommodation training exercises.

According to an alternative embodiment compatible with the preceding alternative embodiments, the second recommendation is to perform a binocular vision assessment.

According to an alternative embodiment compatible with the preceding alternative embodiments, the third recommendation is to suggest an addition with a weak correction value.

According to an alternative embodiment compatible with the preceding alternative embodiments, the fourth recommendation is to suggest an addition with an intermediate correction value.

According to an alternative embodiment compatible with the preceding alternative embodiments, the fifth recommendation is to suggest an addition having a strong correction value.

A second aspect of the invention relates to a device for assessing the near vision accommodative state of a non-presbyopic individual, including;
display means configured to display at least one optotype at a fixed n distance from the individual's eyes;
placement means configured to place optical lenses in front of the individual's eyes;
a storage memory;
a calculator including means configured to perform the steps of the method according to a first aspect of the invention.

According to one embodiment, the display means are configured to display at least one selection suggestion and/or symbol and the device according to a second aspect of the invention includes selection means configured to select a selection suggestion and/or symbol and processing means configured to process the selections.

Thus, the method according to a first aspect of the invention may be implemented by the individual whose accommodative state is being assessed. Indeed, the individual himself or herself selects, via the selection means, the selection suggestion and/or the symbol displayed on the display means and the processing means take these selections into account to sequence the steps of the method.

A third aspect of the invention relates to a computer program product including software instructions which, when the program is executed by a computer, implement the method according to a first aspect of the invention.

A fourth aspect of the invention relates to a computer-readable recording medium on which the computer program product according to a third aspect of the invention is recorded.

The invention and its various applications will be better understood upon reading the following description and upon examining the accompanying figures.

BRIEF DESCRIPTION OF THE FIGURES

The figures are set forth for indicative and in no way limiting purposes of the invention.

FIG. 1 shows a block diagram of a method according to a first aspect of the invention.

FIG. 2 shows a schematic representation of one embodiment of a device according to a second aspect of the invention.

DETAILED DESCRIPTION

Unless otherwise specified, a same element appearing in different figures has a unique reference.

A first aspect of the invention relates to a method for assessing the near vision accommodative state of a non-presbyopic individual.

By "accommodation" it is meant vision focusing, especially by virtue of changes in the curvature of the crystalline lens according to the distance of objects, so as to form a sharp image on the retina.

By "near vision accommodative state of an individual" it is meant the near vision accommodative behaviour of that individual.

By "non-presbyopic individual" it is meant an individual under the age of 40.

The method according to a first aspect of the invention is automatic, that is it is computer-implemented. In particular, its implementation does not require the intervention of a practitioner.

The method according to a first aspect of the invention is performed after an assessment of the individual's far vision. At the end of this assessment, a far vision assessment report is prepared. This report advises or not a near vision assessment for the individual. Even if the far vision assessment report does not advise a near vision assessment, the practitioner may still choose to assess near vision.

The far vision assessment report may, for example, advise a near vision when the individual has near vision complaints and/or when the individual has accommodative spasms during the far vision assessment and/or when the far vision assessment reveals abnormal accommodative behaviour.

FIG. 1 is a block diagram illustrating the sequence of steps 101 to 120 of the method 100 according to a first aspect of the invention.

The first step 101 of the method 100 consists in placing at least one optotype at a fixed distance from the individual's eyes.

By "optotype" it is meant a character or figure used for measuring visual acuity.

For example, the first step 101 consists in placing at least one group of letters corresponding to a minimum acuity of $4/10$ in front of the individual's eyes.

The optotype is for example placed 40 cm from the individual's eyes.

If a first condition C1 is met, that is if the individual fails to read the optotype, the second step 102 of the method 100 is performed.

The second step 102 of the method 100 consists in interrupting the method 100 and generating a near vision assessment report including a first initial recommendation.

The first initial recommendation is, for example, to consult an ophthalmologist and/or to perform a near vision assessment on trial glasses.

If the first condition C1 is not met, the third step 103 of the method 100 is performed.

The third step 103 of the method 100 consists in placing an initial convex lens having a value within the closed range [+0.50; +1.00] dioptres in front of the individual's eyes. The initial lens is then placed between the individual's eyes and the optotype.

If a second condition C2 is met, that is if the individual prefers without the initial lens rather than with the initial lens, the fourth step 104 of the method 100 is performed.

By "the individual prefers without the initial lens rather than with the initial lens" it is meant that the individual experiences less discomfort related to his or her vision without the initial lens than with the initial lens (more comfortable vision without the initial lens).

The fourth step 104 of the method 100 consists in interrupting the method 100 and generating a near vision assessment report including a second initial recommendation.

The second initial recommendation is, for example, to perform accommodation training exercises and/or to perform a binocular vision assessment.

If the second condition C2 is not met and a third condition C3 is met, the fifth step 105 of the method 100 is performed.

The third condition C3 is met if the individual can see no difference with or without the initial lens.

The fifth step 105 of the method 100 consists in removing the initial lens.

If a fourth condition C4 is met, that is, if the individual has an adaptation time to see clearly again after removing the initial lens, the sixth step 106 of the method 100 is performed.

The sixth step 106 of the method 100 consists in placing again the initial lens.

The sixth step 106 of the method 100 is then followed by the eighth step 108 of the method 100.

If the fourth condition C4 is not met and a fifth condition C5 is met, the seventh step 107 of the method 100 is performed.

The fifth condition C5 is met if the far vision assessment report does not advise a near vision assessment.

The seventh step 107 of the method 100 consists in interrupting the method 100 and generating a near vision assessment report.

If the fourth condition C4 is not met and the fifth condition C5 is not met, the sixth step 106 of the method 100 is performed.

The eighth step 108 of the method 100 consists in placing a first convex lens with a value within the closed range [+0.50; +1.00] dioptres in front of the individual's eyes.

If a sixth condition C6 is met, that is, if the individual has blurred vision after placing the first lens, the ninth step 109 of the method 100 is performed.

The ninth step 109 of the method 100 consists in interrupting the method 100 and generating a near vision assessment report including a first recommendation.

The first recommendation is, for example, to perform accommodation training exercises.

If the sixth condition C6 is not met, the tenth step 110 of the method 100 is performed.

The tenth step 110 of the method 100 consists in placing a second convex lens with a value within the closed range [+0.50; +1.00] dioptres in front of the individual's eyes.

If a seventh condition C7 is met, that is, if the individual has blurred vision after placing the second lens, the ninth step 109 of the method 100 is performed.

If the seventh condition C7 is not met, the eleventh step 111 of the method 100 is performed.

The eleventh step 111 of the method 100 consists in placing a third convex lens with a value within the closed range [+0.25; +0.50] dioptres in front of the individual's eyes.

If an eighth condition C8 is met, that is, if the individual has blurred vision after placing the third lens, the ninth step 109 of the method 100 is performed.

If the eighth condition C8 is not met, the twelfth step 112 of the method 100 is performed.

The twelfth step 112 of the method 100 consists in placing a fourth convex lens with a value within the closed range [+0.25; +0.50] dioptres in front of the individual's eyes.

If a ninth condition C9 is met, that is, if the individual has blurred vision after placing the fourth lens, and if the fifth condition C5 is met, the seventh step 107 of the method 100 is performed.

If the ninth condition C9 is met and the fifth condition C5 is not met, the thirteenth step 113 of the method 100 is performed.

The thirteenth step 113 of the method 100 consists in interrupting the method 100 and generating a near vision assessment report including a second recommendation.

The second recommendation is, for example, to perform a binocular vision assessment.

If the ninth condition C9 is not met, the fourteenth step 114 of the method 100 is performed.

The fourteenth step 114 of the method 100 consists in placing a fifth convex lens with a value within the closed range [+0.25; +0.50] dioptres in front of the individual's eyes.

If a tenth condition C10 is met, that is, if the individual has blurred vision after placing the fifth lens and if the fifth condition C5 is met, the seventh step 107 of the method 100 is performed.

If the tenth condition C10 is met and the fifth condition C5 is not met, the fifteenth step 115 of the method 100 is performed.

The fifteenth step 115 of the method 100 consists in interrupting the method 100 and generating a near vision assessment report including a third recommendation.

The third recommendation is, for example, to suggest an addition having a weak correction value. The weak correction is, for example, 0.50 dioptres.

If the tenth condition C10 is not met, the sixteenth step 116 of the method 100 is performed.

The sixteenth step 116 of the method 100 consists in placing a sixth convex lens with a value within the closed range [+0.25; +0.50] dioptres in front of the individual's eyes.

The value of the initial lens and the value of each of the first, second, third, fourth, fifth and sixth lenses are chosen so that the sum of the values of these lenses is equal to the inverse of the fixed distance in metres between the individual's eyes and the optotype.

Thus, for a fixed distance of 40 cm, the sum of the value of the initial lens and the values of the first, second, third, fourth, fifth and sixth lenses is equal to +2.50 dioptres.

If an eleventh condition C11 is met, that is if the individual has blurred vision after placing the sixth lens, and if the fifth condition C5 is met, the seventh step 107 of the method 100 is performed.

If the eleventh condition C11 is met and the fifth condition C5 is not met, the fifteenth step 115 of the method 100 is performed.

If the eleventh condition C11 is not met, the seventeenth step 117 of the method 100 is performed, followed by the eighteenth step 118 of the method 100.

The seventeenth step 117 of the method 100 consists in removing the first, second, third, fourth, fifth and sixth lenses from in front of the individual's eyes.

The eighteenth step 118 of the method 100 consists in placing a first final convex lens of intermediate correction in front of the individual's eyes and then removing the first final lens and placing a second final convex lens of strong correction in front of the individual's eyes.

The intermediate correction corresponds to a correction value strictly lower than that of the strong correction and the weak correction corresponds to a correction value strictly lower than that of the intermediate correction.

The intermediate correction and the strong correction may be chosen from the following values: +0.50 dioptres; +0.75 dioptres; +1.00 dioptres; +1.25 dioptres.

If a twelfth condition C12 is met, that is, if the individual prefers the first final lens to the second final lens or if the individual can see no difference between the first and second final lenses, the nineteenth step 119 of the method 100 is performed.

By "the individual prefers the first final lens to the second final lens", it is meant that the individual experiences less discomfort related to his or her vision with the first final lens than with the second final lens (more comfortable vision with the first final lens).

The nineteenth step 119 of the method 100 consists in generating a near vision assessment report including a fourth recommendation.

The fourth recommendation is, for example, to suggest an addition with the intermediate correction value.

If the twelfth condition C12 is not met, the twentieth step 120 of the method 100 is performed.

The twentieth step 120 of the method 100 consists in generating an assessment report including a fifth recommendation.

The fifth recommendation is, for example, to suggest an addition with a strong correction value.

Throughout the method 100, to validate or not the conditions, the individual chooses between several options. For example, the individual has to choose between the option "I can see the optotype" and the option "I cannot see the optotype" to validate or not the first condition C1. The selections can be made by the individual himself or herself via selection means or by the practitioner or any other person who enters the individual's choice, for example in a console or in a computer.

At the end of the method 100 according to a first aspect of the invention, a near vision assessment report is generated, including conclusions and possibly one n of the previously mentioned recommendations.

The near vision assessment report may also include additional recommendations depending on, for example, the far vision assessment report of the individual.

This near vision assessment report may then be used by the practitioner to suggest a solution adapted to the individual. The practitioner can choose whether or not to follow the recommendation(s) suggested in the near vision assessment report.

For young presbyopes, that is subjects from 40 to 44 years old (inclusive), an alternative of the method 100 according to a first aspect of the invention may be suggested. Thus, if after the third step 103 of the method 100, the individual prefers with the initial lens or if after the fifth step 105 of the method 100, the fourth condition C4 is met or if after the fifth step 105 of the method 100, the fourth condition C4 and the fifth condition C5 are not met, the eighteenth step 118 of the method 100 is performed.

A second aspect of the invention relates to a device for assessing the near vision accommodative state of a non-presbyopic individual.

FIG. 2 shows a schematic representation of the device 200 according to a second aspect of the invention.

The device 200 according to a second aspect of the invention includes a storage memory 203 and a calculator 204 including means configured to perform the steps of the method 100 according to a first aspect of the invention.

The device 200 also includes placement means 202 configured to place optical lenses in front of the individual's eyes.

The placement means 202 are for example an automatic refractor head.

The device 200 also includes display means 201 configured to display at least one optotype at a fixed distance from the individual's eyes.

The display means 201 are for example a screen or a poster.

According to a first embodiment, the display means 201 are also configured to display validation suggestions and/or symbols.

The display means 201 is for example configured to display a symbol for validating that one lens is preferred to another.

The device 200 then also includes selection means 206 configured to select a suggestion and/or symbol, and more precisely to allow user selection of a suggestion and/or symbol, and processing means 205 configured to process the user selections.

The selection means are for example a remote control, a tablet, a console or a microphone.

The processing means 205 are for example a calculator. The processing means 205 are for example included in the calculator 204.

For example, following the third step 103 of the method 100, the display means 201 display a first symbol for choosing the initial lens, a second symbol for choosing without the initial lens, and a third symbol for indicating that there is no difference with or without the initial lens. The individual selects the third symbol by virtue of the selection means 206 and the processing means 205 process the selection of the third symbol to initiate performance of the fifth step 105 of the method 100.

The invention claimed is:
1. A method for automatically assessing the near vision accommodative state of a non-presbyopic individual, the method being performed after an assessment of the individual's far vision has led to the preparation of a far vision assessment report, the method comprising the following steps performed in order:
placing at least one optotype at a fixed distance from the individual's eyes;
   if the individual fails to read the optotype, interrupting the method and generating a near vision assessment report including a first initial recommendation;
placing an initial convex lens with a value within a range [+0.50; +1.00] dioptres in front of the individual's eyes:
   if the individual prefers without the initial lens rather than with the initial lens, interrupting the method and generating a near vision assessment report including a second initial recommendation;
   if the individual can see no difference with or without the initial lens, removing the initial lens:
     if the individual has an adaptation time to see clearly again after removing the initial lens, placing the initial lens;
     otherwise:
       if the far vision assessment report does not advise a near vision assessment, interrupting the method and generating a near vision assessment report;
       otherwise, placing the initial lens;
placing a first convex lens with a value within the range [+0.50; +1.00] dioptres in front of the individual's eyes:
   if the individual has blurred vision after placing the first lens, interrupting the method and generating a near vision assessment report including a first recommendation;
placing a second convex lens with a value within the range [+0.50; +1.00] dioptres in front of the individual's eyes:
   if the individual has blurred vision after placing the second lens, interrupting the method and generating a near vision assessment report including a first recommendation;
placing a third convex lens with a value within a range [+0.25; +0.50] dioptres in front of the individual's eyes:
   if the individual has blurred vision after placing the third lens, interrupting the method and generating a near vision assessment report including a first recommendation;
placing a fourth convex lens with a value within the range [+0.25; +0.50] dioptres in front of the individual's eyes:
   if the individual has blurred vision after placing the fourth lens and:
     if the far vision assessment report does not advise a near vision assessment, interrupting the method and generating a near vision assessment report;
     otherwise, interrupting the method and generating a near vision assessment report including a second recommendation;
placing a fifth convex lens with a value within the range [+0.25; +0.50] dioptres in front of the individual's eyes:
   if the individual has blurred vision after placing the fifth lens and:
     if the far vision assessment report does not advise a near vision assessment, interrupting the method and generating a near vision assessment report;

otherwise, interrupting the method and generating a near vision assessment report including a third recommendation;
placing a sixth convex lens with a value within the range [+0.25; +0.50] dioptres in front of the individual's eyes:
if the individual has blurred vision after placing the sixth lens and:
if the far vision assessment report does not advise a near vision assessment, interrupting the method and generating a near vision assessment report;
otherwise, interrupting the method and generating a near vision assessment report including a third recommendation;
otherwise:
removing the initial lens and the first, second, third, fourth, fifth and sixth lenses;
placing a first final convex lens of intermediate correction in front of the individual's eyes and then removing the first final lens and placing a second final convex lens of strong correction in front of the individual's eyes:
if the individual prefers the first final lens to the second final lens or if the individual can see no difference between the first and second final lenses, generating a near vision assessment report including a fourth recommendation;
otherwise, generating a near vision assessment report including a fifth recommendation.

2. The method according to claim 1, wherein the first initial recommendation is to consult an ophthalmologist and/or to perform a near vision assessment on trial glasses.

3. The method according to claim 1, wherein the second initial recommendation is to perform accommodation training exercises and/or to perform a binocular vision assessment.

4. The method according to claim 1, wherein the first recommendation is to perform accommodation training exercises.

5. The method according to claim 1, wherein the second recommendation is to perform a binocular vision assessment.

6. The method according to claim 1, wherein the third recommendation is to suggest an addition with a weak correction value.

7. The method according to claim 1, wherein the fourth recommendation is to suggest an addition having the intermediate correction value.

8. The method according to claim 1, wherein the fifth recommendation is to suggest an addition having the strong correction value.

9. A device for assessing the near vision accommodative state of a non-presbyopic individual for implementing the method according to claim 1, including:
a display configured to display at least one optotype at a fixed distance from the individual's eyes and to display at least one selection suggestion and/or symbol;
placement means configured to place optical lenses in front of the individual's eyes; and
a storage memory;
a calculator;
selection means configured to select a selection suggestion and/or symbol.

10. A non-transitory computer readable medium comprising machine readable instructions which, when the instructions are executed on a computer, cause the computer to implement the steps of the method according to claim 1.

* * * * *